United States Patent [19]

Cowen

[11] Patent Number: 5,062,417

[45] Date of Patent: Nov. 5, 1991

[54] PROSTHESIS WITH IMPROVED PUMP

[75] Inventor: Timothy B. Cowen, Andover, Minn.

[73] Assignee: Mentor Corporation, Minneapolis, Minn.

[21] Appl. No.: 597,088

[22] Filed: Oct. 10, 1990

[51] Int. Cl.[5] ............................................. A61F 2/26
[52] U.S. Cl. ..................................................... 128/79
[58] Field of Search .......................... 128/79, DIG. 25

[56] References Cited

U.S. PATENT DOCUMENTS

| | | | |
|---|---|---|---|
| 3,272,403 | 9/1966 | Alexander | 222/509 |
| 4,407,278 | 10/1983 | Burton et al. | 128/79 |
| 4,566,446 | 1/1986 | Fogarty | 128/79 |
| 4,782,826 | 11/1988 | Fogarty | 128/79 |

Primary Examiner—O'Connor Cary E.
Attorney, Agent, or Firm—Hugh D. Jaeger

[57] ABSTRACT

A penile prosthesis employing an improved pump and valve system. The main body of the prosthesis has at least one inflatable polymer cylinder suitable for implantation within the corpus cavernosum of the male patient. The penis of the patient is rendered erect by pumping a sterile fluid into the inflatable polymer cylinder(s) under adequate pressure.

The sterile fluid is supplied from a reservoir and pump implanted within the scrotum of the patient which are linked to the inflatable polymer cylinder(s) by flexible tubing. The reservoir is a relatively low pressure flexible polymer bag of relatively large volume. Coupled to the reservoir by a valved diaphragm is a pump having only much less flexible walls and a relatively small volume.

Manual squeezing of the reservoir forces sterile fluid through the valved diaphragm into the pump chamber. Because the walls of the pump are more rigid, the sterile fluid is conveyed under pressure through the tubing to the inflatable polymer cylinder(s) producing the erectile state.

A check valve is located within the inflatable polymer cylinder(s) to prevent premature release of the pressurized sterile fluid, and thus, sustain the erectile state until manual manipulation of the check valve. The released sterile fluid is returned via the flexible tubing to the pump chamber in the scrotum. However, because of its relative rigidity, the sterile fluid exits the pump via the valved diaphragm and returns to the reservoir.

5 Claims, 7 Drawing Sheets

PROSTHESIS WITH IMPROVED PUMP

CROSS REFERENCE TO CO-PENDING APPLICATIONS

This application is related to U.S. patent application Ser. No. 07/522,821 filed May 14, 1990, entitled "Corpus Cavernosum Implant Device"; and U.S. patent application Ser. No. 7/530,339 filed May 30, 1990, entitled "Penile Prosthesis" are commonly assigned to the assignee of the present invention.

BACKGROUND OF THE INVENTION

1. Field of the Invention

The present invention relates generally to implantable medical devices, and more particularly, relates to implantable medical devices for the treatment of male impotence.

2. Description of the Prior Art

Implantable cylinders for the treatment of male impotence have been in use for some time. The more sophisticated of these devices employ fluid systems whereby the cylinder may be evacuated to produce the flaccid state and inflated to produce the erect state.

An early patent disclosing such an implantable system is U.S. Pat. No. 4,009,711, issued to Uson et al., which uses a pair of inflatable cylinders implanted in a corpus cavernosum of the penis. Each of the cylinders include a non-distensible portion of a semi-rigid material to be implanted into the root end of the corpus cavernosum and a pendulous, distensible body portion. The distensible body portion or inflatable cylinder is connected by tubing to a fluid reservoir located in the scrotal sac, and a check valve is provided to control the flow of fluid between the reservoir and the inflatable cylinder. A similar device is disclosed in U.S. Pat. No. 4,235,227, issued to Yamanaka.

A common problem of such early devices is adequate control of the pressurized sterile fluid and volumetric efficiency of the reservoir. U.S. Pat. No. 4,407,278, issued to Burton et al., addresses the control problem by providing the implantable cylinder with a check valve at the distal end. However, Burton et al., are not able to add volumetric efficiency. In fact the difficulty may be compounded by the use of a reservoir at the base of the penis, particularly with the embodiments using a separate pump located within the scrotum.

SUMMARY OF THE INVENTION

The present invention overcomes the disadvantages of the prior art by providing penile prosthesis having an improved system for handling the sterile fluid in the erect state, the flaccid state, and during transitions. This improved handling system is readily employed using a number of cylinder designs, including most especially those which are the subject of the above referenced and commonly assigned U.S. Patent Applications, which are herein incorporated by reference.

The reservoir and pump assembly is a single structure of two chambers adapted for implantation within the scrotum of the patient. The chamber used as the reservoir has the much larger volume when filled (i.e. the system is in the flaccid state). The walls of the reservoir chamber are highly flexible. The second chamber is the pumping chamber. It has a much smaller volume and far more rigid walls. The reservoir chamber and pump chamber are separated by a semiflexible diaphragm containing a slot valve.

Because the reservoir chamber is so flexible, the sterile fluid contained therein is readily pressurized by manual squeezing. The pressurized sterile fluid passes from the reservoir chamber into the pump chamber via the slot valve. This pressure is easily maintained by the pump chamber by the more rigid walls. The pressurized sterile fluid is thus forced through flexible tubing into the inflatable cylinder(s) implanted within the penis. The slot valve in the diaphragm, along with a corresponding check valve at the distal end of the inflatable cylinder(s), ensure that the sterile fluid does not back flow.

When it is desired to return to the flaccid state, manual pressure is applied to the check valve. This causes the pressurized sterile fluid to back flow from the cylinder(s), through the flexible tubing and pump chamber, and into the reservoir chamber by way of the slot valve.

Maximum control of the process is achieved through use of the automatic slot valve and the manually operated check valve. Volumetric efficiency is obtained through the use of the two valves along with the dual chamber reservoir/pump structure.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
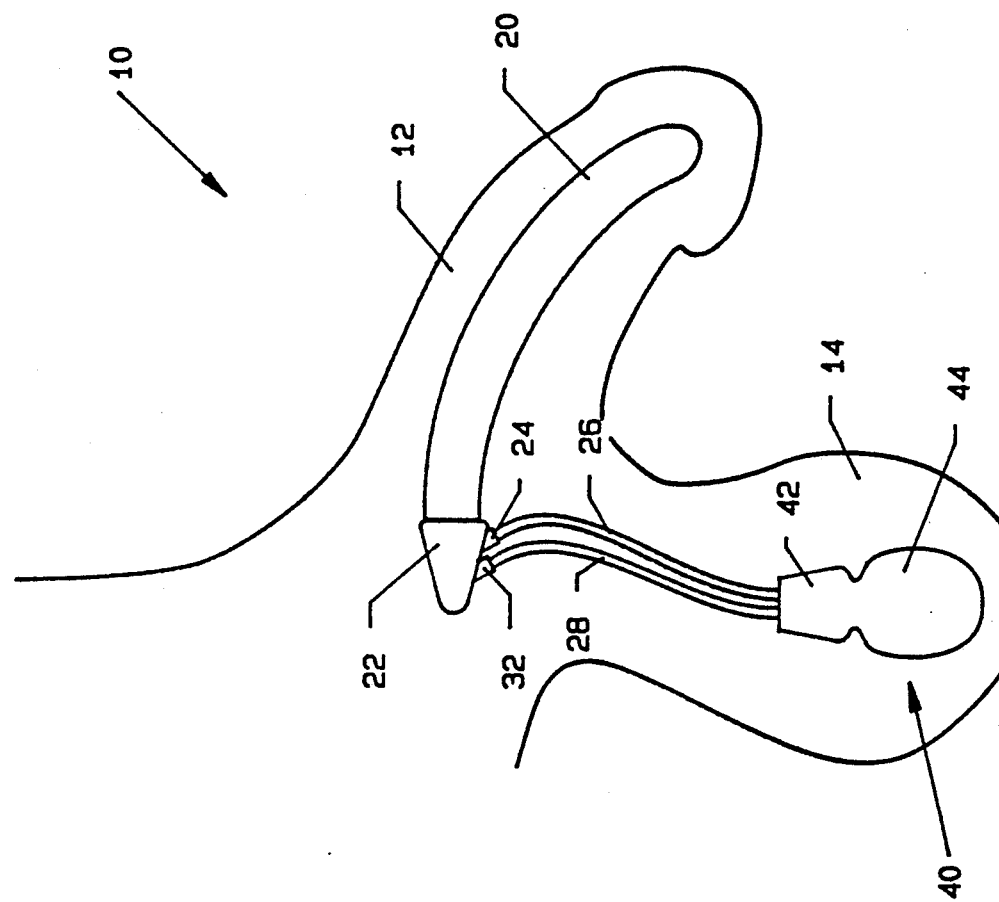
FIG. 1 is a conceptual view of a prosthetic system of the present invention shown in the flaccid state.

FIG. 1 is a conceptual view of a prosthetic system according to the present invention as implanted into a male patient. The reservoir/pump assembly 40 is implanted within scrotum 14. Inflatable cynlinder 20 and inflatable cylinder 30 (not seen in this view) are implanted within the corpus cavernosum of penis 12. Base 22 and base 34 (not shown) are implanted at the base of penis 12 and supply the required mechanical rigidity.

Reservoir/pump assembly 40 consists of two separate chambers. Reservoir chamber 44 has a larger volume and generally flexible walls. Pump chamber 42 has rather rigid walls and a smaller volume.

Inflatable cylinder 20 is in fluid communication with pump chamber 42 via flexible tubing 26 attached to coupling 24. Similarly, flexible tubing 28 and coupling 32 provide fluid communication between pump chamber 42 and inflatable cylinder 30.

Figure 2:
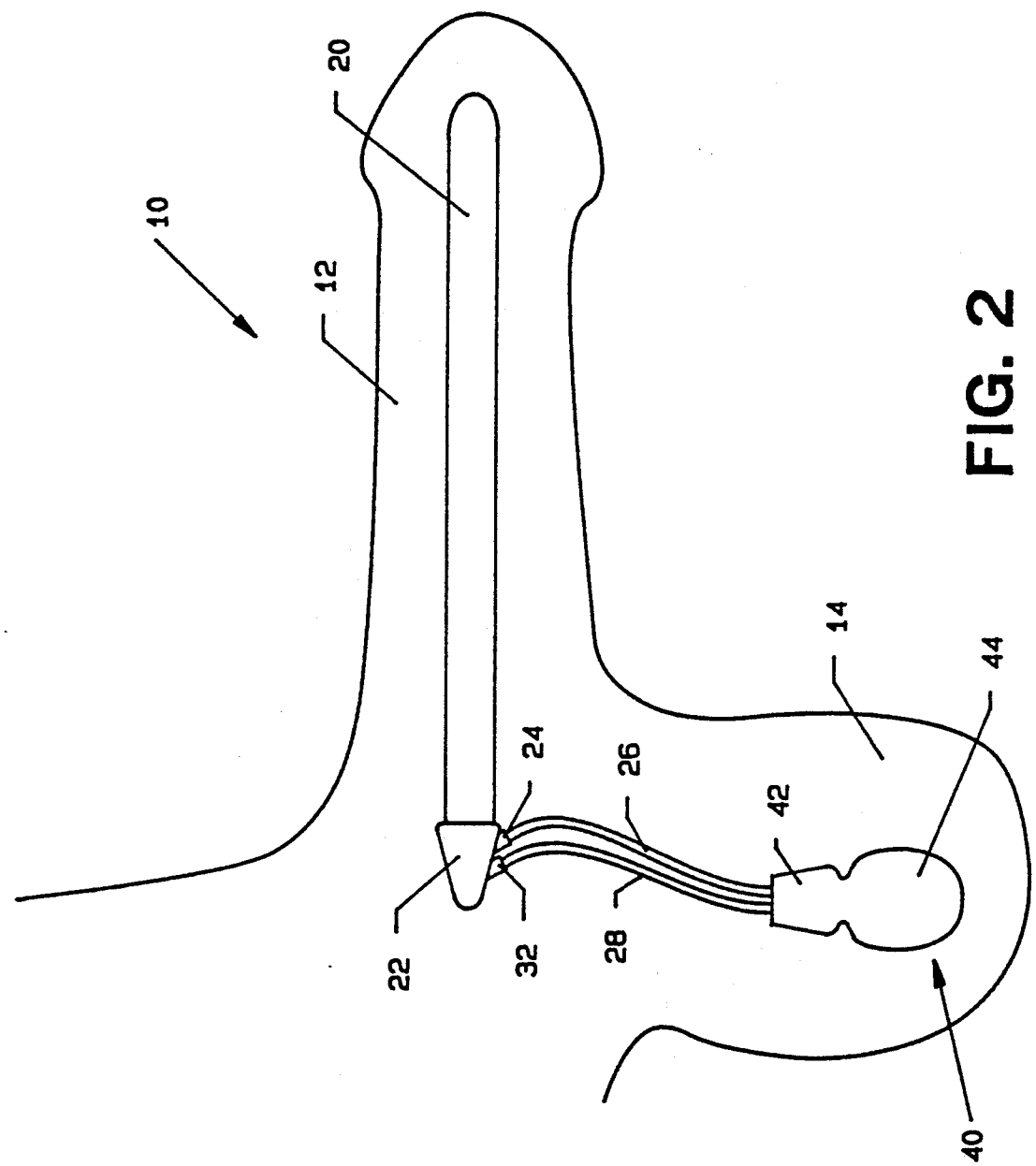
FIG. 2 is a conceptual view of the prosthetic system of the present invention shown in the erect state.

FIG. 2 is a conceptual view of the present invention shown in the erect state. All referenced elements are as previously described.

Figure 3:
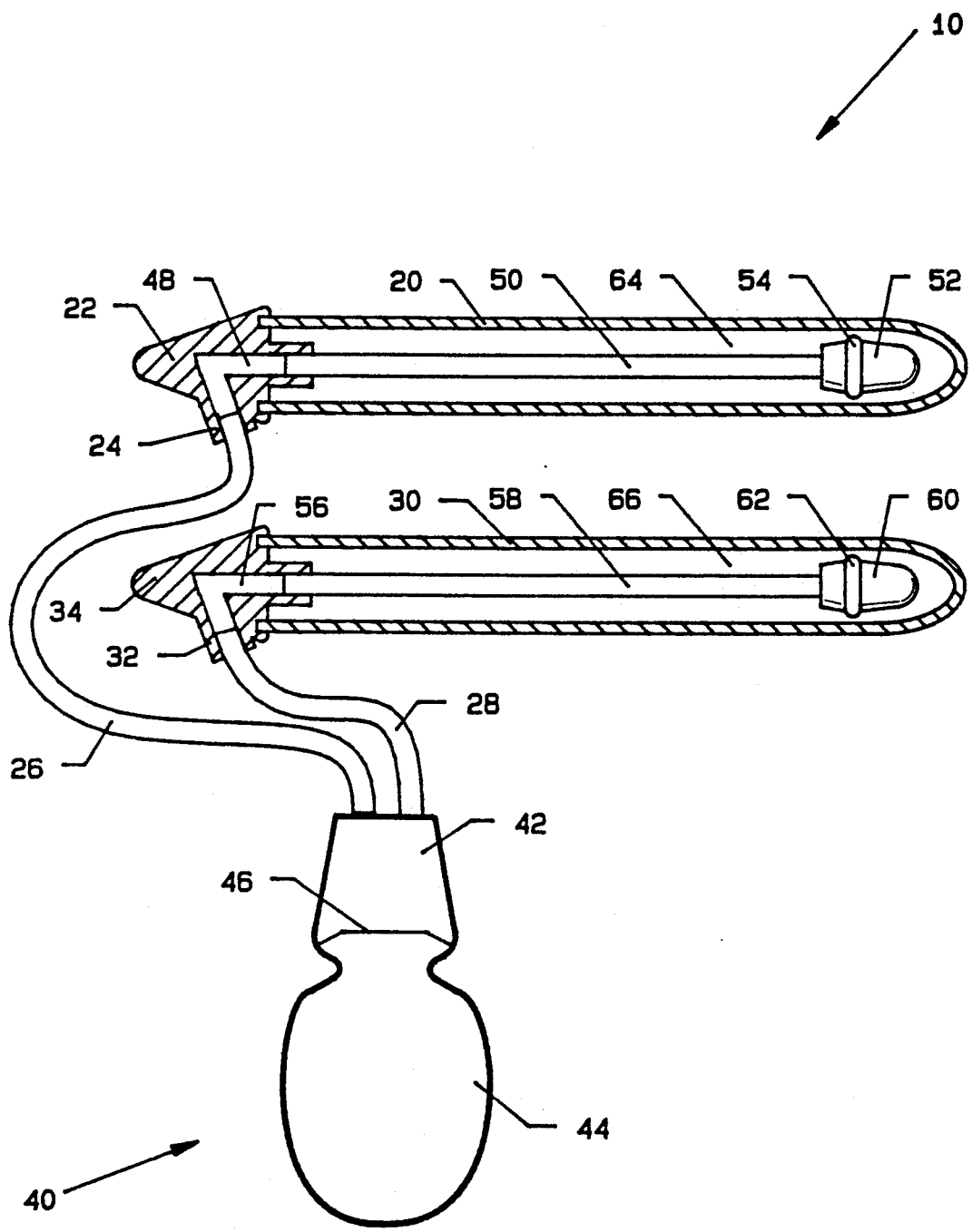
FIG. 3 is a partially sectioned view of the preferred embodiment of the present invention.

FIG. 3 is a sectioned view of prosthetic system 10 employing the present invention. Diaphragm 46 separates pump chamber 42 from reservoir chamber 44. The construction and operation of reservoir/pump assembly 40 is discussed in further detail below.

The cross section shows attachment of inflatable cylinder 20 to base 22. In the preferred mode, inflatable cylinder 20 is formed of a flexible polymer to produce enclosed lumen 64. The proximal end of inflatable cylinder 20 is sealingly coupled to the distal end of base 22, which is molded of a rigid body compatible material such as an implantable polymer.

Flexible tubing 26 is sealingly attached to coupling 24, which is a fluid port molded on base 22. Fluid communication is maintained from flexible tubing 26 through coupling 24 into lumen 48 of base 22. Tubing 50 conveys the sterile fluid to and from the distal end of inflatable cylinder 20. Fluid coupling between tubing 50 and enclosed lumen 64 is controlled by check valve 52. Ridge 54 opens check valve 52 in the proximal direction when manually squeezed. Check valve 52 is normally open in the distal direction.

Inflatable cylinder 30 has a lumen 66 containing tubing 58 and check valve 60 with ridge 62 in similar fashion. Base 34 having lumen 56 in fluid communication with tubing 58 and coupling 32, is sealingly attached to inflatable cylinder 30.

Figure 4:
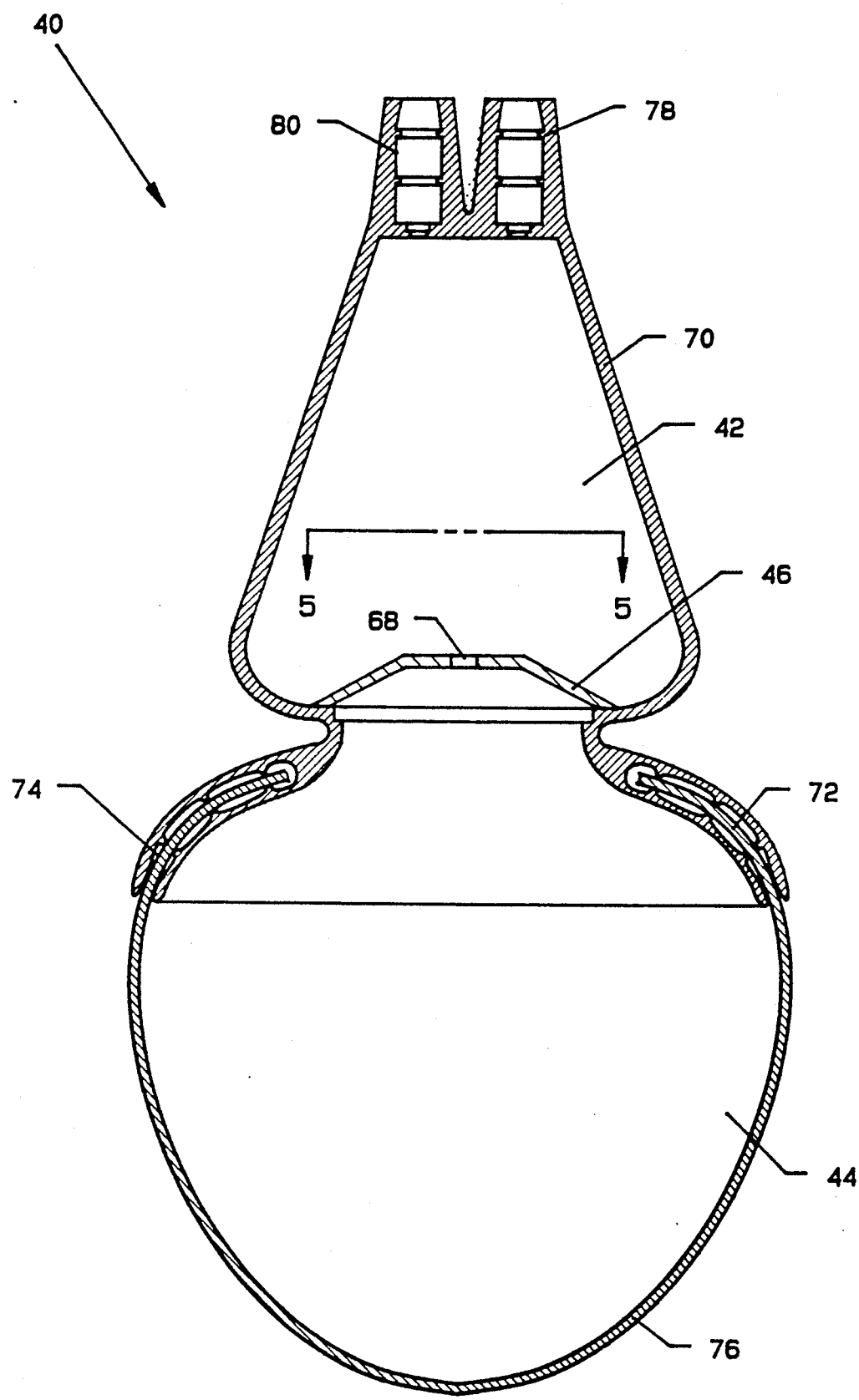
FIG. 4 is a close up sectioned view of the pump and reservoir chambers.

FIG. 4 is a close up sectioned view of reservoir/pump assembly 40. Reservoir chamber 44 has an outer wall 76 of a flexible polymer. In this way, outer wall 76 may be manually squeezed (after implant) to force any sterile fluid (i.e. preferably saline solution) found therein out of reservoir chamber 44 into pump chamber 42. Furthermore, because the entire system is closed to the atmosphere, it is necessary that outer wall 76 collapse to produce a smaller volume within reservoir chamber 44 to compensate for the sterile fluid which is pumped into inflatable cylinders 20 and 30, causing an equal but opposite increase in volume.

On the other hand, pump chamber 42 is defined by rigid wall 70 which is coupled to other wall 76 as shown at points 72 and 74. The volume of pump chamber 42 is smaller than the maximum volume of reservoir chamber 44 and is fixed. This ensures that pressurized sterile fluid entering pump chamber 42 is transferred under equivalent pressure to inflatable cylinders 20 and 30.

Reservoir chamber 44 is separated from pump chamber 42 by diaphragm 46. Though diaphragm 46 is flexible, it is relatively inelastic such that its surface area remains essentially constant under pressure. Slot valve 68 is located within diaphragm 46. As the sterile fluid in reservoir chamber 44 is pressurized by manual force on outer wall 76, diaphragm 46 is directed concavely into pump chamber 42 as shown, and slot valve 68 permits transfer of sterile fluid from reservoir chamber 44 into pump chamber 42. Slot valve 68, however, tends to prevent back flow of the sterile fluid.

Coupling 78 and coupling 80 provide fluid communication and sealing attachment of flexible tubing 26 and 28, respectively.

Figure 5:
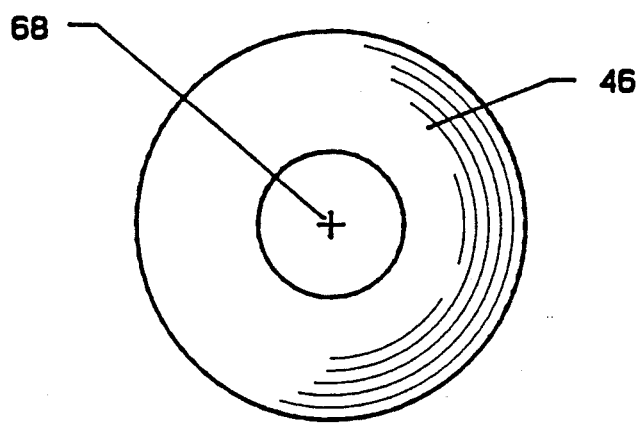
FIG. 5 is a plan view of the diaphragm which separates the pump and reservoir chambers.

FIG. 5 is a top view of diaphragm 46 as seen from pump chamber 42 towards reservoir chamber 44. Note that slot valve 68 has a cross shape.

Figure 6:
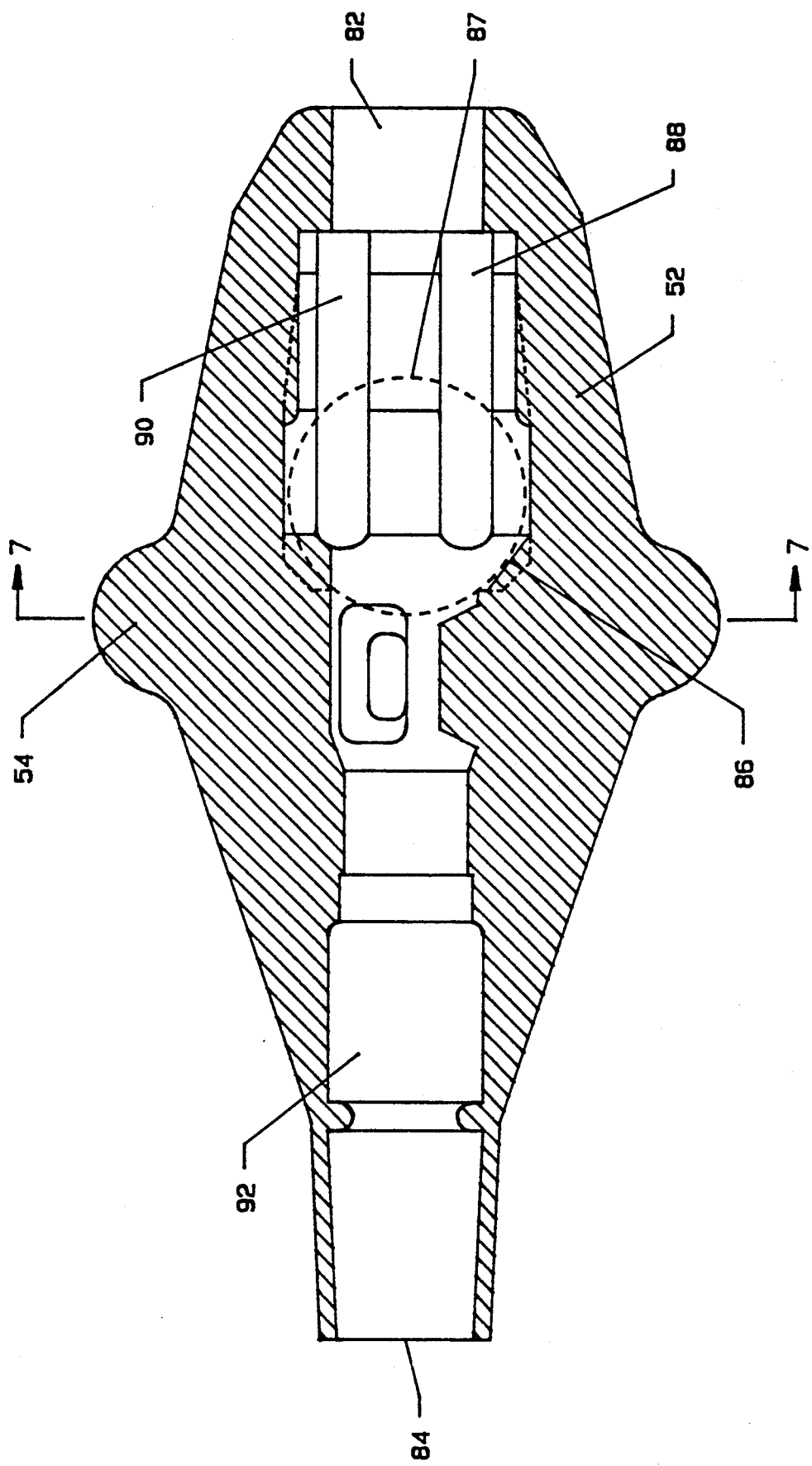
FIG. 6 is a close u sectioned view of the check valve.

FIG. 6 is a sectioned close up side view of check valve 52. As the erect state is entered (i.e. inflatable cylinder 20 is inflated with sterile fluid), sterile fluid is transferred through port 84 into inner lumen 92. Stainless steel sphere within valve passage 86 permits the fluid to pass only in the distal direction in the normal mode. The pressurized sterile fluid passes through valve passage to distal port 82 for inflation of inflatable cylinder 20. Lugs and bars 88 and 90 center stainless steel sphere 87, permitting fluid to flow around the sphere and preventing the sphere from extending under high pressure.

Deflation of inflatable cylinder 20 (i.e. reentry into the flaccid state) is accomplished by manually squeezing ridge 54. This displaces the stainless steel sphere to open valve passage 86 to transfer of sterile fluid in the proximal direction permitting the sterile fluid to be returned to reservoir chamber 44. Inflatable cylinder 30 operates in a similar fashion.

Figure 7:
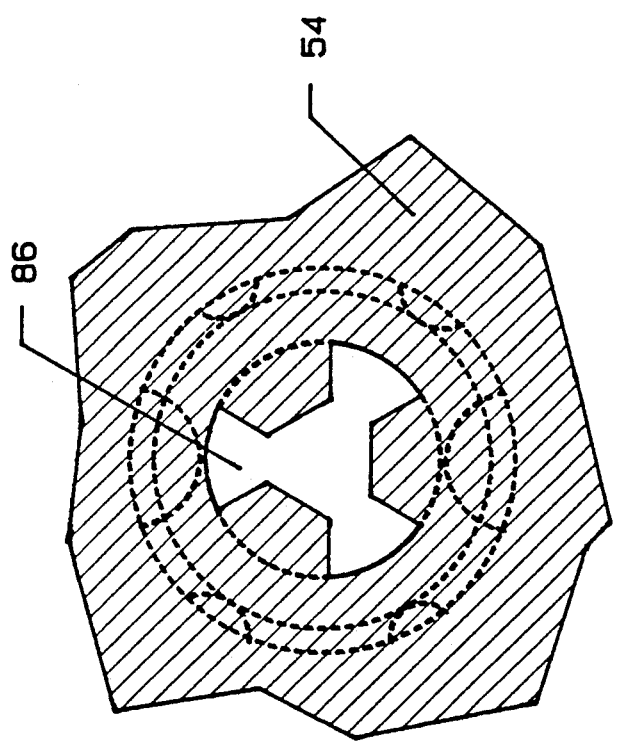
FIG. 7 is a close up sectioned view of the check valve.

FIG. 7 is a close up and cut away view of valve passage 86 as seen in a distal to proximal direction.

Having thus described the preferred embodiments, those of skill in the art will be readily able to apply the teachings found herein to yet other embodiments within the scope of the claims hereto attached.

I Claim:

1. A penile prosthesis comprising:
   a. at least one inflatable cylinder implantable within the corpus cavernosum of a patient;
   b. a reservoir chamber implantable within the scrotum of said patient having a first volume and having a flexible wall;
   c. a pump chamber having a second volume and having a rigid wall fixedly attached to said flexible wall of said reservoir chamber;
   d. means coupled to said at least one inflatable cylinder and said pump chamber for providing fluid communication between said at least one inflatable cylinder and said pump chamber;
   e. means coupled to said providing means for regulating fluid transfer with said providing means; and,
   f. a diaphragm containing a slot valve disposed between said reservoir chamber and said pump chamber for controlling fluid communication between said reservoir chamber and said pump chamber.

2. A penile prosthesis according to claim 1 wherein said second volume is less than said first volume.

3. A penile prosthesis according to claim 2 wherein said regulating means is a ball valve.

4. A penile prosthesis according to claim 3 wherein said regulating means is fixedly attached to said at least one inflatable cylinder.

5. A method of treating impotency of a male patient comprising:
   a. implanting at least one inflatable cylinder in the penis of said male patient;
   b. implanting a two chamber reservoir/pump in fluid communication with said at least one inflatable cylinder within the scrotum of said patient; and,
   c. forcing fluid from a first chamber of said two chamber reservoir/pump through a second chamber of said two chamber reservoir/pump and into said at least one inflatable cylinder.

* * * * *